United States Patent [19]

Papantoniou et al.

[11] 4,070,533
[45] Jan. 24, 1978

[54] TERPOLYMER OF (a) CROTONIC ACID (b) VINYL ACETATE AND (c) ALLYL OR METHALLYL ESTERS

[75] Inventors: Christos Papantoniou, Epinay-sur-Seine; Jean-Claude Grognet, Gagny, both of France

[73] Assignee: L'Oreal, Paris, France

[21] Appl. No.: 674,274

[22] Filed: Apr. 6, 1976

Related U.S. Application Data

[62] Division of Ser. No. 563,461, March 31, 1975, Pat. No. 3,966,404.

[30] Foreign Application Priority Data

Apr. 1, 1974 Luxembourg .......................... 69760

[51] Int. Cl.² .................... C08F 20/04; C08F 8/30; C08F 2/00
[52] U.S. Cl. .................... 526/16; 260/29.6 TA; 526/49; 526/50; 526/200; 526/218; 526/317
[58] Field of Search ............... 526/317, 16, 49, 50, 526/47

[56] References Cited

U.S. PATENT DOCUMENTS 3,231,534  1/1966  Blades et al. .................... 526/185
3,455,887  7/1969  Levine .......................... 526/317
3,484,420  12/1969  Chihara ......................... 526/317
3,579,629  5/1971  Pasero et al. .................... 526/317
3,716,633  2/1973  Viout et al. ..................... 526/317
3,810,977  5/1974  Levine et al. .................... 424/47

*Primary Examiner* — Herbert J. Lilling
*Attorney, Agent, or Firm* — Cushman, Darby & Cushman

[57] ABSTRACT

Terpolymer of crotonic acid, vinyl acetate and an allyl or methallyl ester having the formula

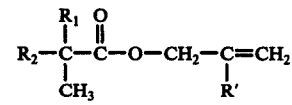

wherein R' is hydrogen or $CH_3$, $R_1$ is a saturated hydrocarbon chain containing 1-6 carbon atoms and $R_2$ is $-CH_3$ or $-CH(CH_3)_2$, with the proviso that the sum of the number of carbon atoms in $R_1 + R_2$ is equal to or less than 7. The terpolymer is employed with a cosmetic carrier or vehicle to provide a cosmetic composition for the hair, such as a hair lacquer or hair setting lotion, generally in amounts of about 1–4 weight percent of the composition.

9 Claims, No Drawings

TERPOLYMER OF (a) CROTONIC ACID (b) VINYL ACETATE AND (c) ALLYL OR METHALLYL ESTERS

This is a division, of application Ser. No. 563,461 filed Mar. 31, 1975, now U.S. Pat. No. 3,966,404.

The present invention relates to new copolymers and particularly to terpolymers which are usefully employed in the production of cosmetic compositions such as hair lacquer or hair setting lotion compositions.

It is known that natural or synthetic resins, most often solubilized in a hydroalcoholic or alcoholic cosmetic carrier, are currently employed to provide hair lacquer or hair setting lotion compositions.

Representative resins and polymers used up to now include, in particular, polyvinylpyrrolidone, copolymers of vinylpyrrolidone and vinyl acetate, copolymers of acrylic esters and unsaturated monocarboxylic acid, copolymers of maleic anhydride and vinyl alkyl ether, copolymers resulting from the copolymerization of vinyl acetate, crotonic acid and other unsaturated monomers such as vinyl esters having from 13–25 carbon atoms and allyl or methallyl esters having from 14 to 27 carbon atoms, as well as copolymers of vinyl acetate, crotonic acid and branched vinyl esters having at least 7 carbon atoms.

With regard to these latter polymers, the terpolymers of the present invention exhibit numerous advantages.

First, the terpolymers of the present invention can be obtained in a more economical manner and with great purity. Moreover, it is possible in accordance with this invention to obtain polymers having a molecular weight clearly lower than those previously produced, without it being necessary to use chain regulating agents. This is quite desirable when the terpolymer is to be used in cosmetics especially since it has been observed that when such chain regulating agents are employed, the resulting copolymer is often contaminated to the point where its use in cosmetic compositions is virtually excluded because of residual odors or because of parasitic reactions which occur between such chain regulated polymers and other components in cosmetic compositions.

Although other methods have been known to regulate the polymer chain, i.e. mass or suspension polymerization which employs significant quantities of initiators, or solution polymerization, these methods are difficult to put into practice and are less economical than the process of the present invention.

According to the present invention, the polymerization of the different comonomers provides, without having to have recourse to chain regulating means, terpolymers having a molecular weight not exceeding 30,000 and such terpolymers in the cosmetic field exhibit significantly quite better qualities than those previously described and currently used in this field.

In effect, the terpolymers according to the present invention have in addition to the cosmetic qualities required for all hair lacquers or hair setting lotions, the long sought after characteristic of being easily removed by brushing and combing of the hair.

Finally the terpolymers of the present invention exhibit excellent solubility in alcohols, such as ethyl or isopropyl alcohol, thereby enabling a reduction, in significant proportions, of the quantity of this type of solvent in the ultimate cosmetic formulation.

The present invention is thus related to an industrial product which comprises a terpolymer resulting from the copolymerization of
(a) crotonic acid,
(b) vinyl acetate and
(c) an allyl or methallyl ester having the formula

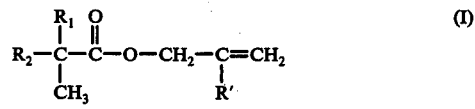

wherein
R' is selected from the group consisting of hydrogen and $CH_3$;
$R_1$ is a saturated linear or branched hydrocabon having 1–6 carbon atoms;
$R_2$ is selected from the group consisting of $-CH_3$ and $-CH(CH_3)_2$, with the proviso that the sum of the number of carbon atoms in $R_1$ and $R_2$ is equal to or less than 7.

Further, in accordance with the present invention the said terpolymers result from the copolymerization of 6–15, preferably 7–12, weight percent crotonic acid, 65–86, preferably 71–83, weight percent vinyl acetate, and 8–20, preferably 10–17, weight percent allyl or methallyl ester of formula I.

Representative allyl or methallyl esters of formula I include allyl dimethyl propanoate, methallyl dimethyl propanoate, allyl 2,2-dimethyl pantanoate, methallyl 2,2-dimethyl pentanoate, allyl 2,2-dimethyl hexanoate, methallyl 2,2-dimethyl hexanoate, allyl 2,2-dimethyl octanoate, methallyl 2,2-dimethyl octanoate, allyl 2-isopropyl-2,3-dimethyl butyrate and methallyl 2-isopropyl-2,3-dimethyl butyrate.

The terpolymers of the present invention have, preferably, a molecular weight ranging between about 15,000 and 30,000.

In a particular embodiment of the present invention, the copolymers are crosslinked with the aid of a crosslinking agent present in an amount between 0.1 – 1.2 weight percent.

Representative crosslinking agents that can be used include diallyl ether diethylene glycol, tetra allyloxyethane, triallyl ether of trimethylol propane, the diacrylates or dimethacrylates of diols such as ethylene glycol.

Crosslinking of the copolymers is particularly recommended when it is desired to obtain terpolymers having a higher viscosity.

In accordance with the present invention the terpolymers can be present in homogeneous or heterogeneous form.

By homogeneous copolymers is meant copolymers whose different macromolecular chains contain substantially the same content of one of the monomers thereof along the entire length of the chains, the content of the said monomer not varying more than 2.5 percent by weight relative to the average content of this monomer for essentially all of the macromolecular chains along the entire length of said chains.

The use of homogeneous terpolymers in the cosmetic composition provides numerous advantages relative to the use of the same polymers but in a heterogeneous form.

In effect the use of homogeneous polymers provides significant cosmetic qualities and notably an absence of powdering of the resin between several applications of aerosol lacquers containing the same to the hair.

The attainment of polymers having a homogeneous composition is a particularly delicate operation and this operation is singularly complicated when the polymer is a terpolymer.

In the case of terpolymers containing vinyl acetate and crotonic acid, the use of an allyl or methallyl ester having a branched hydrocarbon chain is particularly recommended since its presence homogenizes the terpolymer composition during the polymerization reaction.

The present invention has also for an object a new industrial product comprising the terpolymers described above, the acid function of which is neutralized with the aid of an organic base such as monoethanol amine, diethanolamine, triethanolamine, isopropanolamine, morpholine, as well as certain amino alcohols, such as 2-amino-2-methyl-1-propanol and 2-amino-2-methyl-1,3-propanediol.

In accordance with the present invention, the terpolymers can advantageously be neutralized with one of the bases mentioned above in a quantity equal, for example, to 10–150 percent and preferably from 50–120 percent of the quantity corresponding to stoichiometric neutralization.

The terpolymers according to the present invention can be prepared by liquid phase copolymerization, for example in a solvent such as alcohol or benzene. However, it is preferable to carry out the polymerization reaction in mass, or in suspension, in a medium such as water.

The polymerization reaction can be effected in the presence of a polymerization catalyst such as benzoyl peroxide, lauroyl peroxide or azo bis isobutyronitrile, the concentration of the catalyst being between, for example 0.5–6 percent, preferably between 1–4 percent by weight relative to the total weight of the monomers being reacted.

The polymerization in suspension which yields copolymers in the form of pearls is carried out as described above in water and in the presence of a protective colloid such as polyvinyl alcohol or polyacrylic acid or hydroxyethyl cellulose.

The concentration of the protective colloid can be, for example, between 0.1–1 percent by weight relative to the total weight of the monomers being polymerized.

The present invention also relates to a novel industrial product comprising a cosmetic composition characterizeed by the fact that it contains at least one terpolymer, as defined above, optionally neutralized, in solution in an appropriate cosmetic vehicle or carrier.

The cosmetic composition in accordance with the present invention can be, for example, a hair lacquer present or not in the form of an aerosol, a hair setting lotion or a hair treating composition.

As an example, an aerosol hair lacquer composition can be produced by packaging under pressure in an aerosol container, 1–4 weight percent of a terpolymer of the present invention, optionally neutralized; 6–45 and preferably 8–25 weight percent of a lower alkanol; and 54–90 weight percent of a liquidfied gaseous propellant, such as dichlorodifluoromethane and trichlorofluoromethane and mixtures thereof.

Preferably the lower alkanol is ethyl or isopropyl alcohol.

A hair setting lotion composition in accordance with the present invention can be provided by introducing into a hydroalcoholic solution containing about 20–66 percent alcohol, 1–3 weight percent of a terpolymer of the present invention. Preferably, the said terpolymer is neutralized as disclosed above.

The cosmetic composition in accordance with the present invention can also contain conventional cosmetic adjuvants such as perfumes, dyes, preservatives, plasticizers, cationic products, non-ionic products, silicones to improve the brilliance or other cosmetic resins.

The following non-limiting examples illustrate the present invention. Unless otherwise stated, all parts and percentages are by weight.

EXAMPLE 1

Preparation of a copolymer of 10% Crotonic acid, 75% vinyl acetate and 15% allyl dimethyl propanoate.

Into a 500 ml round bottomed flask equipped with a mechanical agitator, a nitrogen lead-in tube, a condenser and a thermometer, there are introduced 75 g of vinyl acetate, 15 g of allyl dimethyl propanoate, 10 g of crotonic acid, 1.2 g of benzoyl peroxide and 200 g of water containing 1.6 g of Cellosize.

The resulting mixture is heated to reflux with agitation for 10 hours. The resulting copolymer is recovered in the form of pearls. Yield — 90%; Acid Index — 67; Viscosit, — 2.0 cp (in 5% solution in dimethylformamide, DMF, at 34.6° C); MW = 24,000 (by osmometry in solution in dioxane).

EXAMPLE 2

The method of Example 1 is repeated except that the following monomers were employed: 10 g of crotonic acid, 75 g of vinyl acetate and 15 g of allyl 2,2-dimethyl pentanoate, in the presence of 2 g of benzoyl peroxide. Yield — 95%; Acid Index — 70; Viscosity — 1.84 cp (5% DMP at 34.6° C).

EXAMPLE 3

The method of Example 1 is repeated except that the following monomers were employed: 10 g of crotonic acid, 80 g of vinyl acetate and 10 g of allyl dimethyl propanoate in the presence of 1.2 g of benzoyl peroxide. Yield — 95%, Acid Index — 76; Viscosity — 2.04 cp (5% DMF at 34.6° C); MW = 22,000.

EXAMPLE 4

The method of Example 1 is repeated except that the following monomers were employed: 10 g of crotonic acid, 78 g of vinyl acetate and 12 g of allyl dimethyl propanoate in the presence of 1.2 g of benzoyl peroxide. Yield — 88%; Acid Index — 71; Viscosity — 2.05 cp (5% DMF at 34.6° C).

EXAMPLE 5

The method of Example 1 is repeated except that the following monomers were employed: 7.5 g of crotonic acid, 77.5 g of vinyl acetate and 15 g of allyl dimethyl propanoate in the presence of 1.2 g of benzoyl peroxide. Yield — 90%; Acid Index — 54; Viscosity — 2.06 cp (5% DMF at 34.6° C).

EXAMPLE 6

The method of Example 1 is repeated except that the following monomers were employed: 8 g of crotonic acid; 77 g of vinyl acetate and 15 g of allyl dimethyl propanoate in the presence of 1.2 g of benzoyl peroxide. Yield — 96%; Acid Index — 53.5; Viscosity — 1.99 cp (5% DMF at 34.6° C); MW = 19,000.

EXAMPLE 7

The method of Example 1 is repeated except that the following monomers were employed: 10 g crotonic acid; 75 g vinyl acetate and 15 g of allyl 2,2-dimethyl octanoate in the presence of 4 g of benzoyl peroxide. Yield — 92%; Acid Index — 72.

EXAMPLE 8

Preparation of a homogeneous terpolymer of 10% crotonic acid, 75% vinyl acetate and 15% allyl dimethyl propanoate.

Into a one liter round bottomed flask equipped with a mechanical agitator, a nitrogen lead-in tube, a condenser and a thermometer, there are introduced 75 g of vinyl acetate, 15 g of allyl dimethyl propanoate, 10 g of crotonic acid, 1.2 g of benzoyl peroxide, 90 g of ethylene glycol and 200 g of water containing 1.6 g of Cellosize.

The resulting mixture is heated to reflux with agitation for 11 hours. Tge resulting copolymer is recovered in the form of pearls. Yield — 85%; Acid Index — 65; Viscosity — 1.84 cp (5% DMF at 34.6° C).

EXAMPLE 9

The method of Example 1 is repeated except that the following monomers were employed: 82 g of vinyl acetate, 10 g of crotonic acid and 8 g of allyl dimethyl propanoate. The amount of benzoyl peroxide used was 1.5 weight percent. Yield — 89%; Acid Index — 67; Viscosity — 2.28 cp (5% DMF at 34.6° C).

EXAMPLE 10

The method of Example 1 is repeated except that the following monomers were employed: 71 g of vinyl acetate, 9 g of crotonic acid and 20 g of allyl dimethyl propanoate, in the presence of 1.2 weight percent benzoyl peroxide. Yield — 90%; Acid Index — 60; Viscosity — 1.66 cp (5% DMF at 34.6° C).

EXAMPLE 11

The method of Example 1 is repeated except that the following monomers were employed: 79 g of vinyl acetate, 8 g of crotonic acid and 13 g of allyl dimethyl propanoate. Yield — 90%; Acid Index — 53; Viscosity — 2.22 cp (5% DMF at 34.6° C).

EXAMPLE 12

The method of Example 2 is repeated except that the following monomers were employed: 73 g of vinyl acetate, 12 g of crotonic acid and 15 g of allyl dimethyl propanoate. Yield — 92%; Acid Index — 79; Viscosity — 1.78 cp (5% DMF at 34.6° C).

EXAMPLE 13

The method of Example 1 is repeated except that the following monomers were employed: 75 g of vinyl acetate, 10 g of crotonic acid and 15 g of allyl dimethyl propanoate, in the presence of 0.6 g of azo bis isobutyronitrile as the polymerization catalyst. Yield — 92%; Acid Index — 69; Viscosity — 1.94 cp (5% DMF at 34.6° C); MW = 18,500.

EXAMPLE 14

The method of Example 2 is repeated except that the following monomers were employed: 75 g of vinyl acetate, 12 g of crotonic acid and 13 g of methallyl dimethyl propanoate. Yield — 89%; Acid Index — 80; Viscosity — 1.99 cp (5% DMF at 34.6° C).

EXAMPLE 15

The method of Example 2 is repeated except that the following monomers were employed: 77 g of vinyl acetate, 8 g of crotonic acid and 15 g of methallyl dimethyl propanoate. Yield — 82%; Acid Index — 54; Viscosity — 2.04 cp (5% DMF at 34.6° C).

EXAMPLE 16

The method of Example 2 is repeated except that the following monomers were employed: 75 g of vinyl acetate, 10 g of crotonic acid and 15 g of methallyl 2,2-dimethyl pentanoate. Yield — 83%; Acid Index — 67; Viscosity — 1.85 cp (5% DMF at 34.6° C).

EXAMPLE 17

The method of Example 2 is repeated except that the following monomers were employed: 77 g of vinyl acetate, 8 g of crotonic acid and 15 g of methallyl 2,2-dimethyl pentanoate. Yield — 85%; Acid Index — 52; Viscosity — 2.10 cp (5% DMF at 34.6° C).

EXAMPLE 18

The method of Example 2 is repeated except that the monomers employed were: 75 g of vinyl acetate, 10 g of crotonic acid and 15 g of methallyl 2,2-dimethyl octanoate. Yield — 86%; Acid Index — 67; Viscosity — 1.75 cp (5% DMF at 34.6° C).

EXAMPLE 19

The method of Example 2 is repeated except that the following monomers were employed: 77 g of vinyl acetate, 8 g of crotonic acid and 15 g of methallyl 2,2-dimethyl octanoate. Yield — 84%; Acid Index — 55; Viscosity — 1.83 cp (5% DMF at 34.6° C).

EXAMPLE 20

The method of Example 2 is repeated except that the following monomers were employed: 75 g of vinyl acetate, 10 g of crotonic acid and 15 g of allyl 2-isopropyl-2,3-dimethyl butyrate. Yield — 82%; Acid Index — 67; Viscosity — 1.80 cp (5% DMF at 34.6° C).

EXAMPLE 21

The method of Example 2 is repeated except that the following monomers were employed: 75 g of vinyl acetate, 10 g of crotonic acid and 15 g of methallyl 2-isopropyl-2,3-dimethyl butyrate. Yield — 87%; Acid Index — 67; Viscosity — 1.78 cp (5% DMF at 34.6° C).

EXAMPLE 22

Preparation of a crosslinked copolymer.

Into a two liter three-necked bottle fitted with an agitator, a thermometer, a nitrogen lead-in tube and a reflux condenser there is introduced an aqueous solution composed of 300 parts of distilled water and 2.4 parts of hydroxyethyl cellulose. To this solution there is added a mixture of monomers and polymerization catalyst in a solution composed of 231 parts of vinyl acetate, 24 parts of crotonic acid, 45 parts of allyl dimethyl propanoate, 1.5 parts of diallylether diethyleneglycol and 10.8 parts of benzoyl peroxide.

The resulting mixture is polymerized with agitation at a temperature between 50–100° C for a period ranging from 8–20 hours. The resulting copolymer in the form of pearls is filtered from the reaction mixture, washed and dried. The yield of dry pearls achieved ranges between 90-95°%. The viscosity of the copolymer in a 5% solution in DMF ranges between 1.9-2 cps at 34.6° C.

EXAMPLE 23

The method of Example 22 is repeated except that the monomers employed were provided in a mixture composed of 231 part of vinyl acetate, 24 parts of crotonic acid, 45 parts of allyl dimethyl propanoate, 3 parts of diallylether diethyleneglycol and 10.8 parts of benzoyl peroxide. The resulting crosslinked copolymer has a viscosity of 3.65 cps at 35° C. EXAMPLES OF USE

EXAMPLE 24

A hair composition in accordance with the present invention is prepared by admixing the following components:

| Polymer prepared in accordance with Example 1 | 8 g |
|---|---|
| 2-amino-2-methyl-1,3-propanediol, q.s.p. | pH 7 |
| Ethyl alcohol, q.s.p. | 100 g |

25 g of the above solution are packaged in an aerosol container, under pressure, together with 45 g of trichlorofluoromethane and 30 g of dichlorodifluoromethane.

Additional hair lacquer compositions are prepared in an essentially similar manner except that the polymer of Example 1 is replaced by the polymer prepared in each of Examples 8 through 13, in essentially equivalent amounts.

EXAMPLE 25

A hair setting lotion in accordance with the present invention is prepared by admixing the following components:

| Polymer prepared in accordance with Example 1 | 2 g |
|---|---|
| 2-amino-2-methyl-1-propanol, q.s.p. | pH 7 |
| Ethyl alcohol | 45 g |
| Water, q.s.p. | 100 g |

Additional hair setting lotion compositions are prepared in an essentially similar manner except that the polymer of Example 1 is replaced by the polymer prepared in each of Examples 14 through 18, in essentially equivalent amounts.

EXAMPLE 26

A hair lacquer composition in accordance with the present invention is prepared by admixing the following components:

| Polymer prepared in accordance with Example 4 | 3 g |
|---|---|
| 2-amino-2-methyl-1,3-propanediol, q.s.p. | pH 7 |
| Perfume | 0.1 g |
| Ethyl alcohol, q.s.p. | 12 g |

The resulting solution is packaged in an aerosol container, under pressure, together with 49.7 g of trichlorofluoromethane and 35.3 g of dichlorodifluoromethane. Additional hair lacquer compositions are prepared in an essentially similar manner except that the polymer of Example 4 is replaced by the polymer in each of Examples 7 and 19 in essentially equivalent amounts.

EXAMPLE 27

A hair lacquer composition in accordance with the present invention is prepared by admixing the following components:

| Polymer prepared in accordance with Example 5 | 3 g |
|---|---|
| 2-amino-2-methyl-1,3-propanediol, q.s.p. | pH 7 |
| Perfume | 0.1 g |
| Ethyl alcohol, q.s.p. | 12 g |

The resulting solution is packaged in an aerosol container, under pressure, together with 49.7 g of trichlorofluoromethane and 35.3 g of dichlorofluoromethane.

A similar hair lacquer composition is prepared by replacing the ethyl alcohol with an essentially equivalent amount of isopropyl alcohol.

EXAMPLE 28

A hair lacquer composition in accordance with the present invention is prepared by admixing the following components:

| Polymer prepared in accordance with Example 5 | 2 g |
|---|---|
| 2-amino-2-methyl-1,3-propanediol, q.s.p | pH 7 |
| Perfume | 0.1 g |
| Ethyl alcohol, q.s.p. | 8 g |

The above resulting solution is packaged in an aerosol container, under pressure, together with 52.7 g of trichlorofluoromethane and 37.3 g of dichlorodifluoromethane.

EXAMPLE 29

A hair lacquer composition in accordance with the present invention is prepared by admixing the following components:

| Polymer prepared in accordance with Example 6 | 2 g |
|---|---|
| 2-amino-2-methyl-1,3-propanediol, q.s.p. | pH 7 |
| Perfume | 0.1 g |
| Ethyl alcohol | 8 g |

The above resulting solution is packaged in an aerosol container, under pressure, together with 59 g of trichlorofluoromethane and 31 g of dichlorodilfuoromethane.

EXAMPLE 30

A hair lacquer composition in accordance with the present invention is prepared by admixing the following components:

| Polymer prepared in accordance with Example 3 | 3 g |
|---|---|
| 2-amino-2-methyl-1,3-propanediol, q.s.p. | pH 7 |
| Perfume | 0.1 g |
| Ethyl alcohol | 12 g |

The above resulting solution is packaged in an aerosol container, under pressure, together with 54 g of trichlorofluoromethane and 31 g of dichlorodifluoromethane.

EXAMPLE 31

A hair setting lotion composition in accordance with the present invention is prepared by admixing the following components:

| | |
|---|---|
| Polymer prepared in accordance with Example 20 | 1.8 g |
| Isopropanol amine, q.s.p. | pH 7 |
| Ethyl alcohol | 35 g |
| Water | 100 g |

Similar hair setting lotion compositions are prepared by replacing the polymer of Example 20 with an essentially equivalent amount of the polymers made in accordance with Example 22 and Example 23.

EXAMPLE 32

A hair lacquer composition in accordance with the present invention is prepared by admixing the following components:

| | |
|---|---|
| Polymer prepared in accordance with Example 21 | 2.5 g |
| Diethanolamine, q.s.p | pH 7 |
| Perfume | 0.08 g |
| Isopropyl alcohol, q.s.p. | 9 g |

The above resulting solution is packaged in an aerosol container, under pressure, together with 52.7 g of trichlorofluoromethane and 37.3 g of dichlorodifluoromethane.

EXAMPLE 33

A hair lacquer composition in accordance with the present invention is prepared by admixing the following components:

| | |
|---|---|
| Polymer prepared in accordance with Example 22 | 2.2 g |
| 2-amino-2-methyl-1,3- | 0.147 g |
| Ethyl alcohol | 14 g |
| Perfume | 0.2 g |

The above resulting solution is packaged in an aerosol container, under pressure, together with 51.3 g of trichlorofluoromethane and 32.15 g of dichlorodifluoromethane.

What is claimed is:

1. Terpolymer of
   a. crotonic acid,
   b. vinyl acetate and
   c. an allyl or methallyl ester of the formula $$R_2-\underset{\underset{CH_3}{|}}{\overset{\overset{R_1}{|}}{C}}-\overset{\overset{O}{\|}}{C}-O-CH_2-\underset{\underset{R'}{|}}{C}=CH_2$$

wherein
R' is selected from the group consisting of hydrogen and —CH$_3$,
R$_1$ is a saturated hydrocarbon chain, linear or branched, having 1-6 carbon atoms, and
R$_2$ is selected from the group consisting of —CH$_3$ and —CH(CH$_3$)$_2$, with the proviso that the sum of the number of carbon atoms in R$_1$ and R$_2$ is equal to or less than 7.

2. The terpolymer of claim 1 wherein said crotonic acid is present in an amount of 6-15 weight percent, said vinyl acetate is present in an amount of 65-86 weight percent and said allyl or methallyl ester is present in an amount of 8-20 weight percent.

3. The terpolymer of claim 1 wherein said crotonic acid is present in an amount of 7-12 weight percent, said vinyl acetate is present in an amount of 71-83 weight percent and said allyl or methallyl ester is present in an amount of 10-17 weight percent.

4. The terpolymer of claim 1 wherein said allyl or methallyl ester is selected from the group consisting of allyl dimethyl propanoate, methallyl dimethyl propanoate, allyl 2,2-dimethyl pentanoate, methallyl 2,2dimethyl pentanoate, allyl 2,2-dimethyl hexanoate, methallyl 2,2-dimethyl hexanoate, allyl 2,2-dimethyl octanoate, methallyl 2,2-dimethyl octanoate, allyl 2-isopropyl-2,3-dimethyl butyrate and methallyl 2-isopropyl-2,3-dimethyl butyrate.

5. The terpolymer of claim 1 having a molecular weight ranging between about 15,000 to 30,000.

6. The terpolymer of claim 1 characterized by the fact that it is a homogeneous terpolymer.

7. The terpolymer of claim 1 neutralized with a base selected from the group consisting of monoethanolamine, diethanolamine, triethanolamine, isopropanolamine, morpholine, 2-amino-2-methyl-1-propanol and 2-amino-2-methyl-1,3-propanediol.

8. A process for preparing a terpolymer comprising copolymerizing in an aqueous suspension in the presence of an effective amount of a polymerization catalyst, monomers consisting of crotonic acid, vinyl acetate and an allyl or methallyl ester having the formula $$R_2-\underset{\underset{CH_3}{|}}{\overset{\overset{R_1}{|}}{C}}-\overset{\overset{O}{\|}}{C}-O-CH_2-\underset{\underset{R'}{|}}{C}=CH_2$$

wherein R' is selected from the group consisting of hydrogen and —CH$_3$, R$_1$ is a saturated hydrocarbon chain, linear or branched, having 1-6 carbon atoms and R$_2$ is selected from the group consisting of —CH$_3$ and —CH(CH$_3$)$_2$, with the proviso that the sum of the number of carbon atoms in R$_1$ and R$_2$ is equal to or less than 7.

9. The process of claim 8 wherein said polymerization catalyst is present in an amount ranging from about 0.5-6 percent by weight relative to the total weight of said monomers.

* * * * *